(12) United States Patent
Carlson

(10) Patent No.: US 11,361,105 B2
(45) Date of Patent: Jun. 14, 2022

(54) TIME BLOCKING NOISING FOR DE-IDENTIFICATION

(71) Applicant: KONINKLIJKE PHILIPS N.V., Eindhoven (NL)

(72) Inventor: Eric Thomas Carlson, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 485 days.

(21) Appl. No.: 16/544,253

(22) Filed: Aug. 19, 2019

(65) Prior Publication Data

US 2020/0065524 A1 Feb. 27, 2020

Related U.S. Application Data

(60) Provisional application No. 62/723,041, filed on Aug. 27, 2018.

(51) Int. Cl.
*G06F 21/00* (2013.01)
*G06F 21/62* (2013.01)
*G06F 16/23* (2019.01)
*G16H 10/60* (2018.01)
*H04L 67/12* (2022.01)

(52) U.S. Cl.
CPC ...... *G06F 21/6254* (2013.01); *G06F 16/2365* (2019.01); *G16H 10/60* (2018.01); *H04L 67/12* (2013.01)

(58) Field of Classification Search
CPC ............. G06F 21/6254; G06F 16/2365; G06F 16/2477; G16H 10/60; G16H 10/00; H04L 67/12
See application file for complete search history.

(56) References Cited

U.S. PATENT DOCUMENTS

| 2009/0077148 | A1 | 3/2009 | Yu et al. |
| 2009/0083544 | A1* | 3/2009 | Scholnick ............. H04L 9/3231 713/186 |
| 2013/0339359 | A1 | 12/2013 | Goyal et al. |
| 2014/0056333 | A1* | 2/2014 | Neff ...................... H04B 1/7073 375/149 |
| 2015/0339496 | A1 | 11/2015 | El Amam et al. |
| 2016/0012193 | A1* | 1/2016 | Almogy ................. G16H 50/20 705/3 |

(Continued)

OTHER PUBLICATIONS

Neamatullah, et al., "BMC Medical Informatics and Decision Making", BMC Informatics and Decision Making 2008, 8:32, pp. 1-17.

(Continued)

*Primary Examiner* — Mahfuzur Rahman

(57) ABSTRACT

Techniques disclosed herein relate to removing potentially identifying features of a specific subject from a data set to prevent re-identification of the subject using an external data source. In various embodiments, the data set contains, as potential identifying features of the specific subject, multiple bursts of temporally-proximate events. Time blocks within the data set can be identified to capture one or more of the bursts of temporally-proximate events for the specific subject. Adding random time shifts for each time block can add noise to the data set and remove or obfuscate the identifying features of a specific subject to generate a time shifted data set.

20 Claims, 8 Drawing Sheets

(56) References Cited

U.S. PATENT DOCUMENTS

2016/0154978 A1    6/2016   Baker et al.
2017/0177907 A1    6/2017   Scaiano et al.

OTHER PUBLICATIONS

Yeniterzi, et al., "Effects of personal identifier resynthesis on clinical text de-identification", J AM Med Inform Assoc 2010:17: pp. 159-168.

* cited by examiner

TIME BLOCKING NOISING FOR DE-IDENTIFICATION

RELATED APPLICATION

This application claims priority to and the benefit of U.S. Provisional Application Ser. No. 62/723,041, filed Aug. 27, 2018, which is incorporated by reference herein in its entirety.

TECHNICAL FIELD

Various embodiments described herein are directed generally to de-identification of data. More particularly, but not exclusively, various methods and apparatus disclosed herein relate to de-identifying identifying features of a subject in data.

BACKGROUND OF THE INVENTION

As technology advances, more and more data is being collected, e.g., from the "internet of things," as well as from more specialized data sources such as health care equipment and personnel. As data collection and proliferation becomes more and more ubiquitous, it becomes increasingly important to anonymize various types of protected data while also allowing the data to be leveraged to its full potential. For example, various types of data may be subjected to de-identification or anonymization processing in which data that are usable to identify an individual or group may be scrubbed while other data may be maintained in some form so that it can be used for various beneficial purposes, such as research, data analytics, etc.

As one example, an increasing need exists for large data sets for training machine learning models (such as deep learning neural network models). This has created an increasing pressure to release data sets containing potentially sensitive data (e.g., healthcare data, consumer data, etc.). Standards, such as the Health Insurance Portability and Accountability Act of 1996 (HIPAA) include a minimum level of de-identification required for sensitive data to reduce privacy risks to individuals. However, current standards may be insufficient to prevent re-identification of individuals in de-identified data.

HIPAA standards for de-identification specify that all elements of dates related to an individual must be removed for a data set to be considered de-identified. Current methods to meet this standard often select a reference date (e.g., the date of a first hospital admission for each patient) and replace the date data with an alternative date within the data set for each event. For example, the dates can be replaced with a future date (e.g., the year 2100) for the first hospital admission and future hospital admissions can be determined relative to this future date.

SUMMARY OF THE INVENTION

The present disclosure is directed to methods and apparatus for removing potentially identifying features of a specific subject from data to prevent re-identification of the subject using an external data source. In many cases, there is still a pattern of activity in traditionally de-identified data sets that may be matched to an external data source (e.g., credit card activity, streaming video activity, gas station activity, etc.) which can allow re-identification of the subject. For example, temporal gaps in credit card activity may be used in conjunction with hospital admission data of the subject (also referred to herein as a person) to identify the subject, e.g., by matching the temporal gaps in credit card activity with corresponding temporal gaps in de-identified hospital admission data.

In some embodiments, time blocks containing bursts of temporally-proximate events can be identified within a data set. These burst of temporally-proximate events can indicate, for example, various data collected for a person during a hospital admission. Events can include pieces of data collected during the hospital admission such as: a medical order, a recorded vital sign, a lab result, an applied treatment, waveform data from continuous monitoring devices, etc. In various embodiments, data sets can contain, for example, data collected from multiple hospital admissions for the same person, hospital admissions for multiple people, etc. In some such embodiments, each burst of temporally-proximate events for a specific person (e.g., events during a hospital admission) can be identified as an independent time block within the data set.

In various embodiments, identified time blocks can be randomly shifted. This random shift can preserve the relationship between events within a time block while, at the same time, preventing potentially identifying information in the time block from being matched with an external data source. In other words, the gaps between time blocks are no longer useful for re-identification, but the sequence of events within a time block can still be useful for analytics (e.g., hospital admission data can still be useful for medical analytics).

Techniques disclosed herein relate to removing potentially identifying features of a specific subject from a data set to prevent re-identification of the subject using an external data source. In various embodiments, the data set contains, as potential identifying features of the specific subject, multiple bursts of temporally-proximate events. Time blocks within the data set can be identified to capture one or more of the bursts of temporally-proximate events for the specific subject. Adding random time shifts for each time block can add noise to the data set and remove or obfuscate the identifying features of a specific subject to generate a time shifted data set.

Generally, in one aspect, a method may include: obtaining data indicative of the data set, wherein the data set contains, as potential identifying features of the specific subject, multiple bursts of temporally-proximate events; processing the data indicative of the data set to identify a plurality of time blocks within the data set, wherein each time block in the plurality of time blocks captures one of the bursts of temporally-proximate events for the specific subject; calculating a random time shift for each time block in the plurality of time blocks, wherein the time shift calculated for each time block adds noise between the each time block and one or more temporally-adjacent time blocks of the plurality of time blocks while preserving temporal relationships between individual events of the temporally-proximate events captured in the respective time block, thereby removing or obfuscating the identifying features of the specific subject from the data set; and generating a time shifted data set by applying the random time shifts to events captured in the plurality of time blocks.

In various embodiments, the method may further include the time shifted data set is unmatchable with data indicative of an external data source comprising one or more additional identifying features of the specific subject.

In various embodiments, the method may further include processing the data indicative of the data set to determine the plurality of time blocks by determining one or more time gaps using a predetermined threshold time value, where no events in the bursts of temporally-proximate events occur during each gap in the one or more time gaps. In various embodiments, the method may further include determining a time stamp for each event in the one or more bursts of temporally-proximate events; determining a first time-stamped event after each gap in the one or more gaps to indicate a start of a time block in the plurality of time blocks; determining a last time-stamped event before each gap in the one or more gaps to indicate an end of a time block in the plurality of time blocks; and determining each time bock in the data indicative of the data set using the start of the time block and the end of the time block. In various embodiments, the method may further include calculating the random time shift for each time block in the plurality of time blocks further comprises determining a maximum time shift size, wherein the maximum time shift size is twice a maximum size between the time stamps for each event in the one or more bursts of temporally-proximate events. In various embodiments, the method may further include calculating the random time shift for each block in the plurality of time blocks further comprises interpolating the random time shift for each of the one or more time blocks to generate a block shift function. In various embodiments, the method may further include calculating the random time shift for each of the plurality of time blocks by processing each time block in the one or more time blocks with the block shift function by iterating through each event in the burst of temporally-proximate events to generate a time shift value for each event; and processing each time block in the plurality of time blocks by adding to each event, the time shift value for each event. In various embodiments, the method may further include adding a same time shift value generated by the block shift function to each individual event in one time block in the plurality of time blocks.

In addition, some implementations include at least one non-transitory computer-readable medium comprising instructions that, in response to execution of the instructions by one or more processors, cause one or more processors to perform any of the aforementioned methods. Some implementations also include one or more processors and memory operably coupled with the one or more processors, wherein the memory stores instructions that, in response to the execution of the instructions by one or more processors, cause the one or more processors to perform any of the aforementioned methods.

In addition, some embodiments include one or more processors of one or more computing devices, where the one or more processors are operable to execute instructions stored in associated memory, and where the instructions are configured to cause performance of any of the aforementioned methods. Some embodiments also include one or more non-transitory computer readable storage media storing computer instructions executable by one or more processors to perform any of the aforementioned methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein. These and all other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION OF THE INVENTION

Figure 1:
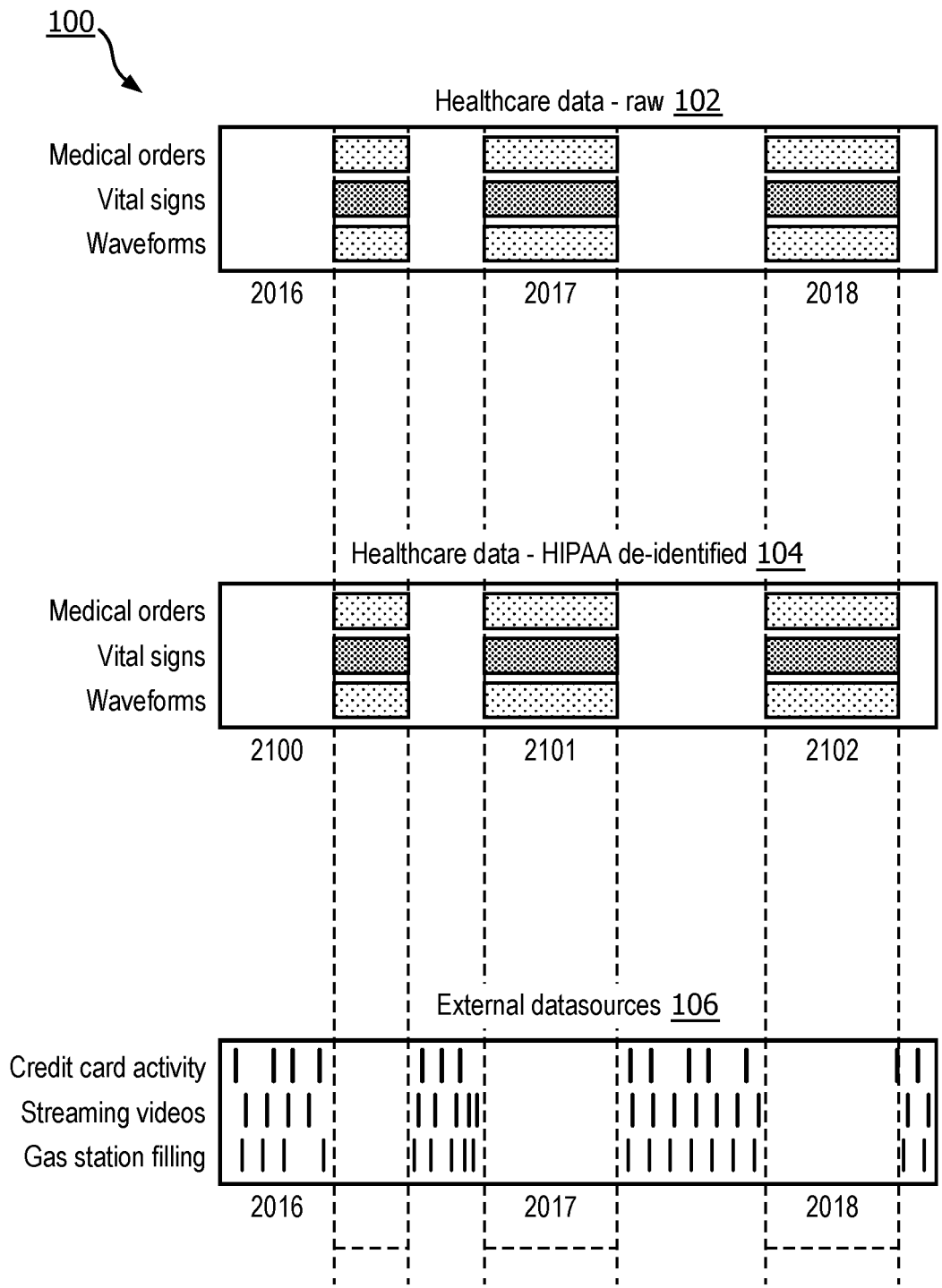
FIG. 1 is a diagram illustrating a comparison of a de-identified data set with data from an external data source, in accordance with an embodiment of the invention.

Several existing models can de-identify a subject within a data set. In medical analytics, it can be necessary to maintain tight timing during periods of acute care (e.g., a hospital stay), while the amount of time between these periods can be less critical. In many embodiments, time sensitive periods (e.g., hospital stays for medical analytics) can be referred to as "time blocks". Time blocks can be identified by periods of relatively high activity that include what will be referred to herein as "bursts" of temporally-proximate events.

In a variety of embodiments, time blocks can be extracted from a data set in several ways. A time stamp from all events in a data set can be extracted for a specific user. For example, time stamps for healthcare data such as medical orders, vital signs, waveforms, etc. can be extracted from a healthcare data set. In some embodiments, event time stamps from different data types can optionally be consolidated into a single data set. In other words, time stamps for medical orders, vital signs, waveforms, etc. in healthcare data can be combined into a single data set. In some embodiments, the difference between each time stamp can be calculated. A time block can be generated by identifying gaps within the data set. In several embodiments, a specified maximum time between events (e.g., user specified, system default, etc.) can be compared with the difference between event time stamps to identify gaps. The first event after a gap can be the start of a time block. Similarly, the last event before a gap can be the end of a time block. Additionally or alternatively, a minimum average event rate can be specified (e.g., user specified, system default, etc.). The number of event time stamps in a specific widow (e.g., an hour window, a one day window, a three day window, a five day window, etc.) can be compared with the minimum average event rate to determine gaps. The first event after a gap can be the start of a time block and the last event before a gap can be the end of a time block.

In various embodiments, a random and/or pseudorandom time shift can be generated for each identified time block. In some embodiments, a time shift can be controlled by a maximum shift to avoid merging time blocks. For example, a time shift can be a system default, a user specified maximum shift, etc. In some embodiments, a time shift can be no longer than twice the minimum time between any two sequential events in the data set. A time shift can optionally be constrained in additional ways. For example, a time shift can be limited to one day increments to preserve time of day information in the data set, one week increments to preserve the day of the week in the data set, etc. In various embodiments, events can occur between time blocks (e.g., a primary care physician visit between time blocks which indicate hospital admissions). In some such embodiments, time shifts can be connected with interpolated time differences (e.g., linear interpolation, sinusoidal interpolation, etc.) to ignore events between time blocks to generate a block shift functions. In many embodiments, block shift functions can be piecewise linear functions.

In some embodiments, a block shift function can be applied to a data set by iterating through every event, comparing the event time with the block shift function to determine a time shifting value, and adding the shifting value to the event time stamp. Events within the same time block will have the same time shifting value. In other words, all events within an individual time block will be shifted the same amount so the timing of events within a time block can still be used in data analytics. In many embodiments, the resulting time shifted data set cannot be exactly matched with any external data sets, thus preventing re-identification of the data while still being useful for analysis.

Referring to FIG. 1, an example image 100 illustrates potential re-identification of a de-identified data set using an external data source. Time runs from left to right in FIG. 1 and in other Figures herein. Image 100 contains raw healthcare data 102 where raw data can contain potentially identifying information. For example, raw healthcare data can contain date and/or time information associated with a variety of collected events such as medical orders, vital signs, waveforms, etc., collected from continuous devices, etc. De-identified healthcare data 104 contains the same medical orders, vital signs, waveforms, etc. but dates have been changed to de-identify the data. For example, raw healthcare data 102 begins in the year 2016. De-identified healthcare data 104 begins at year 2100. Additional dates in the raw healthcare data are shifted to match with 2100 as the initial year for the entire data set. For example, in the de-identified healthcare data set, 2016 becomes 2100, 2017 becomes 2101, 2018 becomes 2102, etc. Image 100 further illustrates external data sources 106 which can potentially be matched with de-identified healthcare data 104 to re-identify the subject. In various embodiments, external data sources can include any data not included in the de-identified healthcare data set including: credit card activity, online streaming video activity, gas station activity, social networking activity, etc. Matching inactivity of a known subject in an external data source with periods of activity in a de-identified data set can re-identify a subject. For example, a subject can be re-identified by matching periods of inactivity in credit card activity with hospital admissions.

Figure 2:
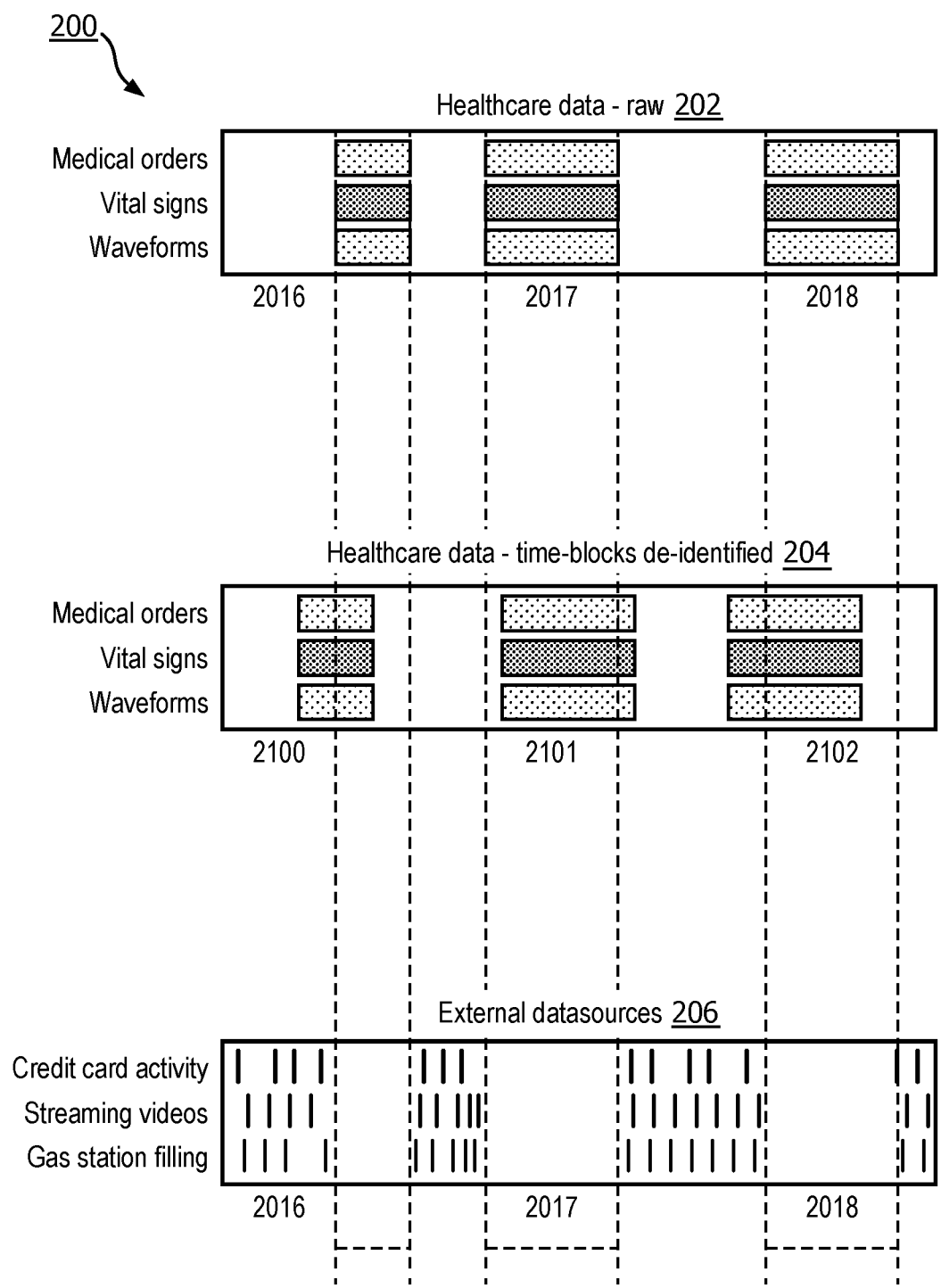
FIG. 2 is a diagram illustrating a comparison of a time shifted de-identified data set with data from an external data source, in accordance with an embodiment of the invention.

FIG. 2 illustrates an example of time shifted de-identified time blocks generated using techniques described herein, in accordance with various embodiments. Image 200 of FIG. 2 illustrates raw healthcare data 202 and external data sources 206 similar to raw healthcare data 102 and external data sources 106 described with respect to FIG. 1. However, de-identified healthcare data 104 as illustrated in FIG. 1 has been replaced with time shifted de-identified healthcare data 204. Time blocks within raw healthcare data 202 which match up with gaps in activity external data sources 206 have been randomly shifted in accordance with various embodiments to generate time shifted de-identified healthcare data 204. Time shifted data sets are unmatchable with potentially identifying features in external data sources 206. In a variety of embodiments, time shifted data can additionally be further de-identified. For example, years can be changed in a time shifted de-identified data set in a way similar to how years are changed to future dates as illustrated in de-identified healthcare data 104 in FIG. 1.

Figure 3:
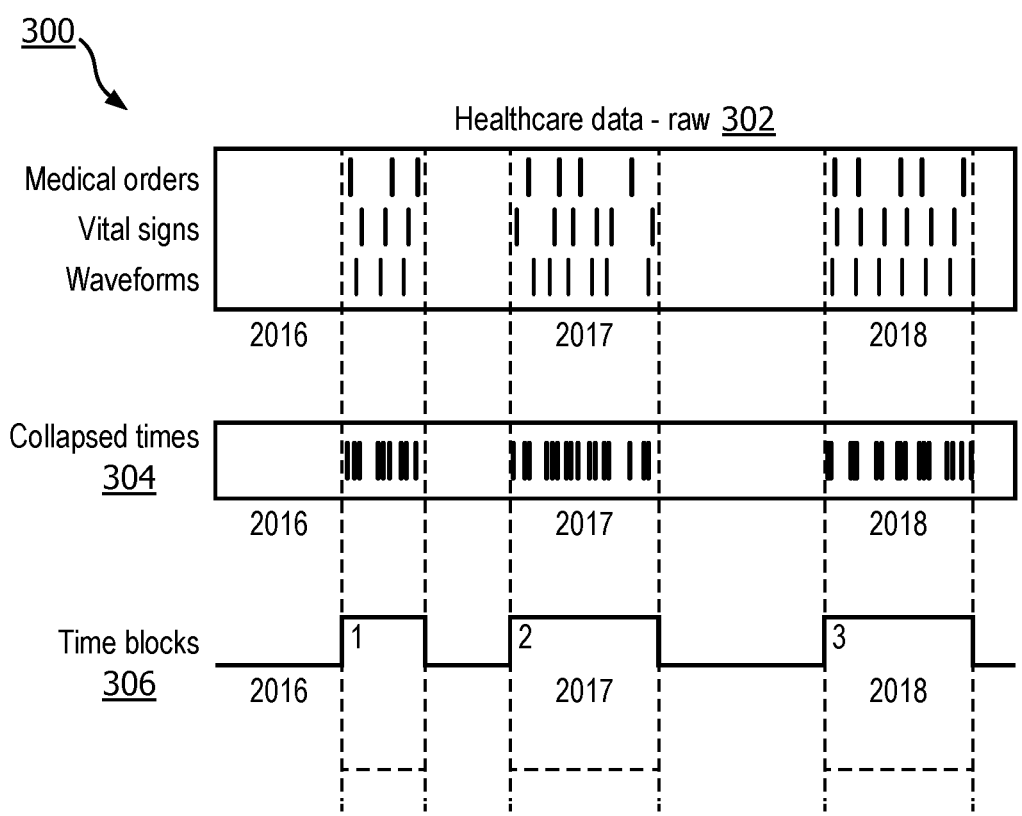
FIG. 3 is a diagram illustrating time block identification, in accordance with an embodiment of the invention.

FIG. 3 illustrates an example of time block identification in accordance with various embodiments. Image 300 of FIG. 3 illustrates raw healthcare data 302 where time stamps for events (indicated by the individual vertical lines) have been extracted. In various embodiments, collapsed times 304 can contain time stamps for different types of events in a data set combined into a single data structure. Three "bursts" of temporally-proximate events are evident in collapsed times 304. In various embodiments, time blocks 306 can be identified within a data set, e.g., from the detected bursts, using event time stamps in raw healthcare data 302 and/or collapsed times 304. Determining time blocks in accordance with various embodiments is illustrated in process 600 in FIG. 6.

Figure 4:
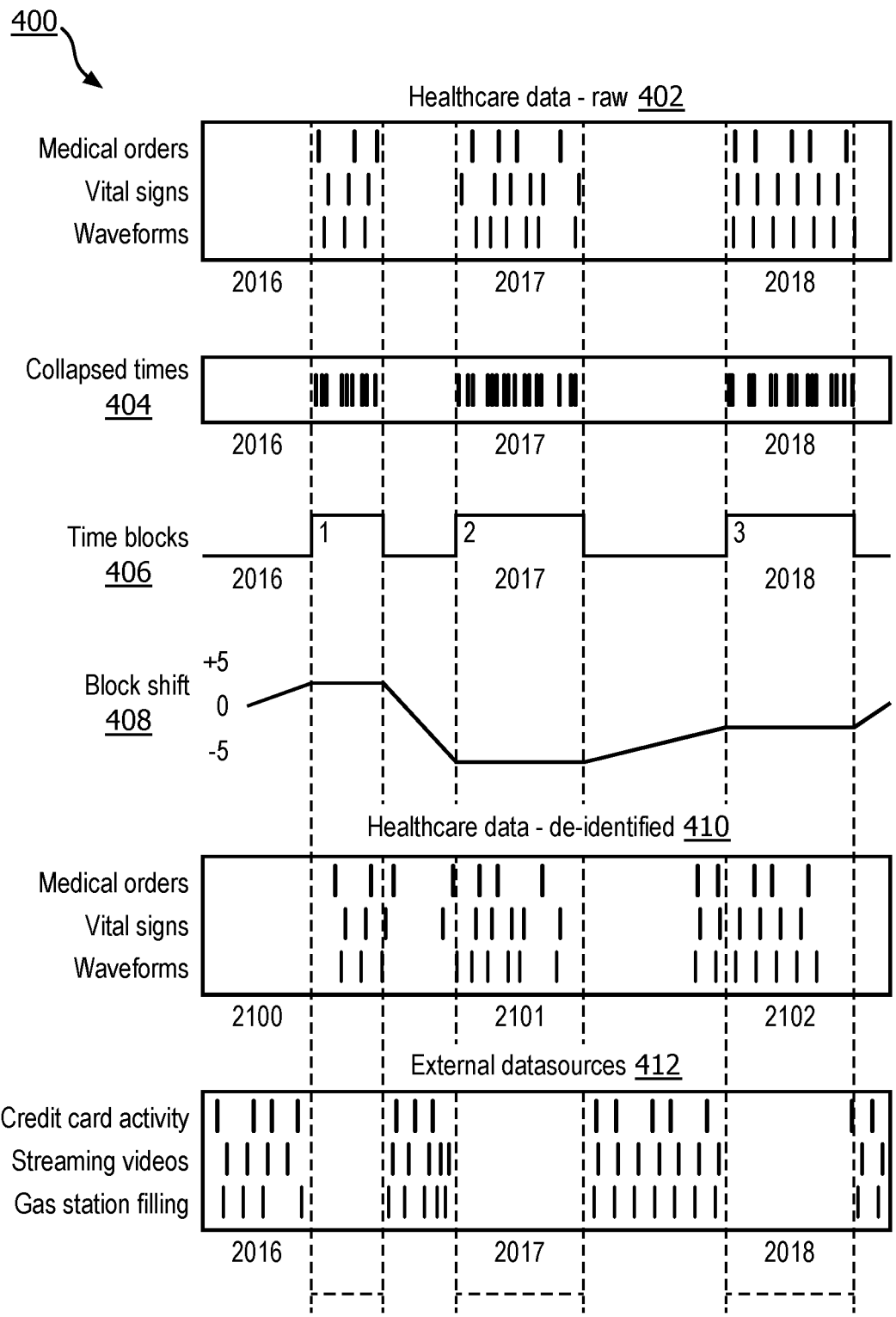
FIG. 4 is a diagram illustrating time block shifting, in accordance with an embodiment of the invention.

FIG. 4 illustrates an example of time block shifting in accordance with various embodiments. Image 400 of FIG. 4 includes raw healthcare data 402 where time stamps for events have been identified similar to raw healthcare data 302 in FIG. 3. In many embodiments, collapsed times 404, similar to collapsed times in 304 illustrated in FIG. 3, can combine time stamps in raw healthcare data 402. Time blocks 406 can be identified from bursts of temporally-proximate events detected in the raw healthcare data 402 and/or collapsed times 404.

In a variety of embodiments, a block shift function 408 can be applied to time blocks 408. In some such embodiments, block shift function 408 can randomly shift time blocks to generate a data set unmatchable with external data sources 412. In a variety of embodiments, block shift function 408 can be a piecewise linear function. In some such embodiments, a piecewise linear block shift function can generate time shifted de-identified healthcare data 410. Determining a block shift function in accordance with various embodiments is described in process 700 in FIG. 7.

Figure 5:
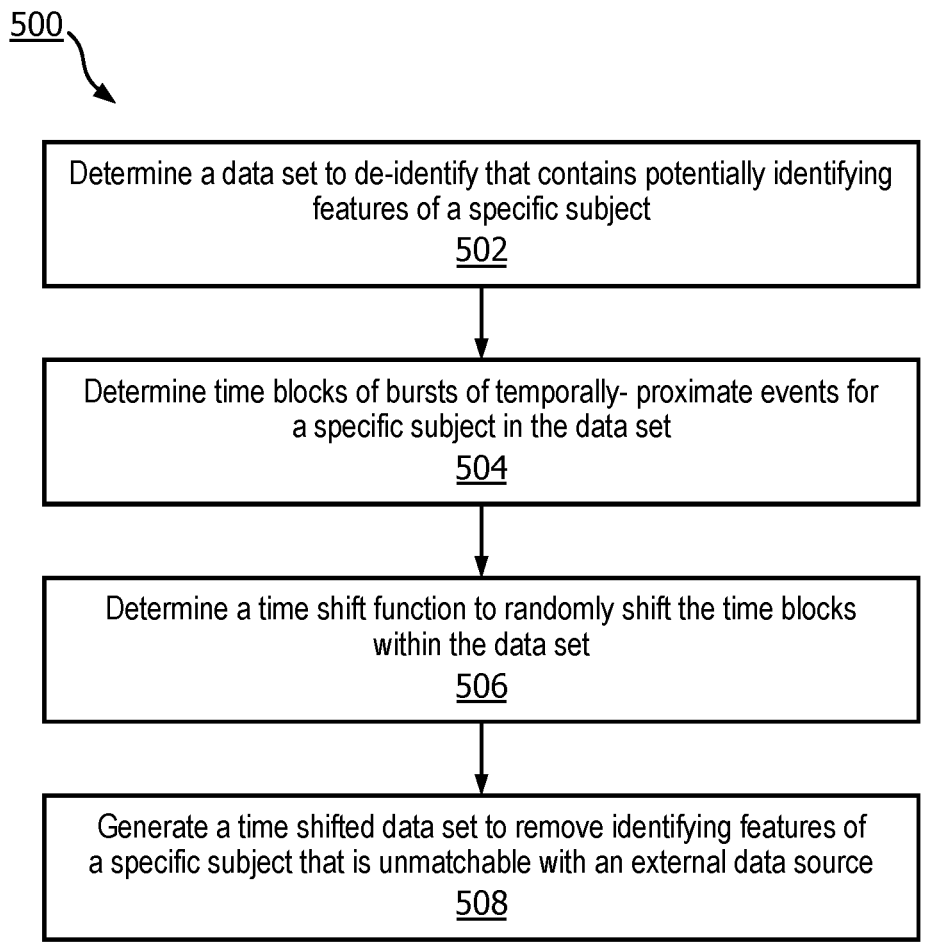
FIG. 5 is a flowchart illustrating an example process of performing selected aspects of the present disclosure, in accordance with an embodiment of the invention.

Referring to FIG. 5, an example process 500 for practicing selected aspects of the present disclosure, in accordance with various embodiments is disclosed. For convenience, the operations of the flowchart are described with reference to a system that performs the operation. This system may include various components of various computer systems, including those described in FIG. 8. Moreover, while operations of process 500 are shown in a particular order, this is not meant to be limiting. One or more operations may be reordered, omitted, and/or added.

At block 502, a data set to de-identify containing potentially identifying features of a specific subject can be determined. For example, events in a medical data set can include medical orders, vital signs, waveform data from continuous monitoring devices, etc.

At block 504, time blocks containing bursts of temporally-proximate events can be determined for a specific subject in the data set. Determining time blocks in accordance with many embodiments is described in process 600 in FIG. 6.

At block 506, a time shift function can be determined to randomly shift the time blocks within the data set. Determining a time shift function in accordance with various embodiments is described in process 700 of FIG. 7.

At block 508, a time shifted data set can be generated where identifying features of a specific subject can be removed making the time shifted data set unmatchable with an external data source.

Figure 6:
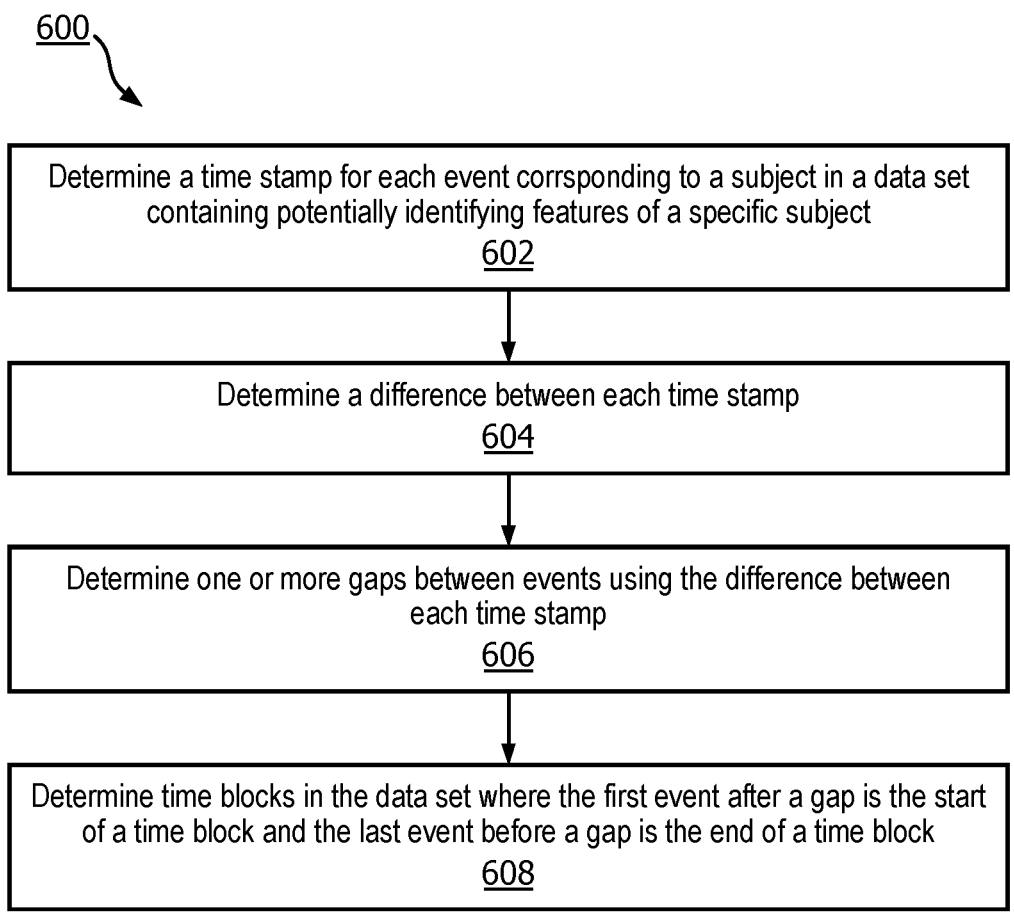
FIG. 6 is a flowchart illustrating another example process for performing selected aspects of the present disclosure, in accordance with an embodiment of the invention.

Referring to FIG. 6, an example process 600 for practicing selected aspects of the present disclosure, in accordance with various embodiments is disclosed. For convenience, the operations of the flowchart are described with reference to a system that performs the operation. This system may include various components of various computer systems, including those described in FIG. 8. Moreover, while operations of process 600 are shown in a particular order, this is not meant to be limiting. One or more operations may be reordered, omitted, and/or added.

At block 602, a time stamp for each event corresponding to a particular subject can be determined in a data set containing potentially identifying features of a specific subject. As an example, FIG. 3 illustrates raw healthcare data 302 with identified time stamps for events. In some embodiments, all time stamps for a specific subject can optionally be collapsed into the same data structure. As an example, collapsed times 304 illustrate events from a data set optionally being combined in a single data structure.

At block 604, a difference between each time stamp can be determined. A difference can be determined between time stamps in a "raw" data set and/or a data structure containing time stamps for all events in a data set. In some embodiments, the difference between sequential time stamps can be determined. In other embodiments, the difference can be determined between a time stamp of an event and time stamps for all other events. At block 606, one or more gaps between a burst of temporally proximate events can be determined using the difference between each time stamp.

In many embodiments, a specified maximum time between events (e.g., a user specified maximum, a system default maximum, etc.) can be compared with the difference between each time stamp to determine gaps. Additionally or alternatively, a minimum average event rate (e.g., a user specified minimum, a system default minimum, etc.) can be compared with the number of events within a predetermined time window to determine gaps in the data set.

At block 608, time blocks in the data set can be determined where the first event after a gap is the start of a time block and the last event before a gap is the end of a time block. For example, time blocks 306 illustrated in FIG. 3 depict time blocks determined based the relationship between event time stamps and gaps.

Figure 7:
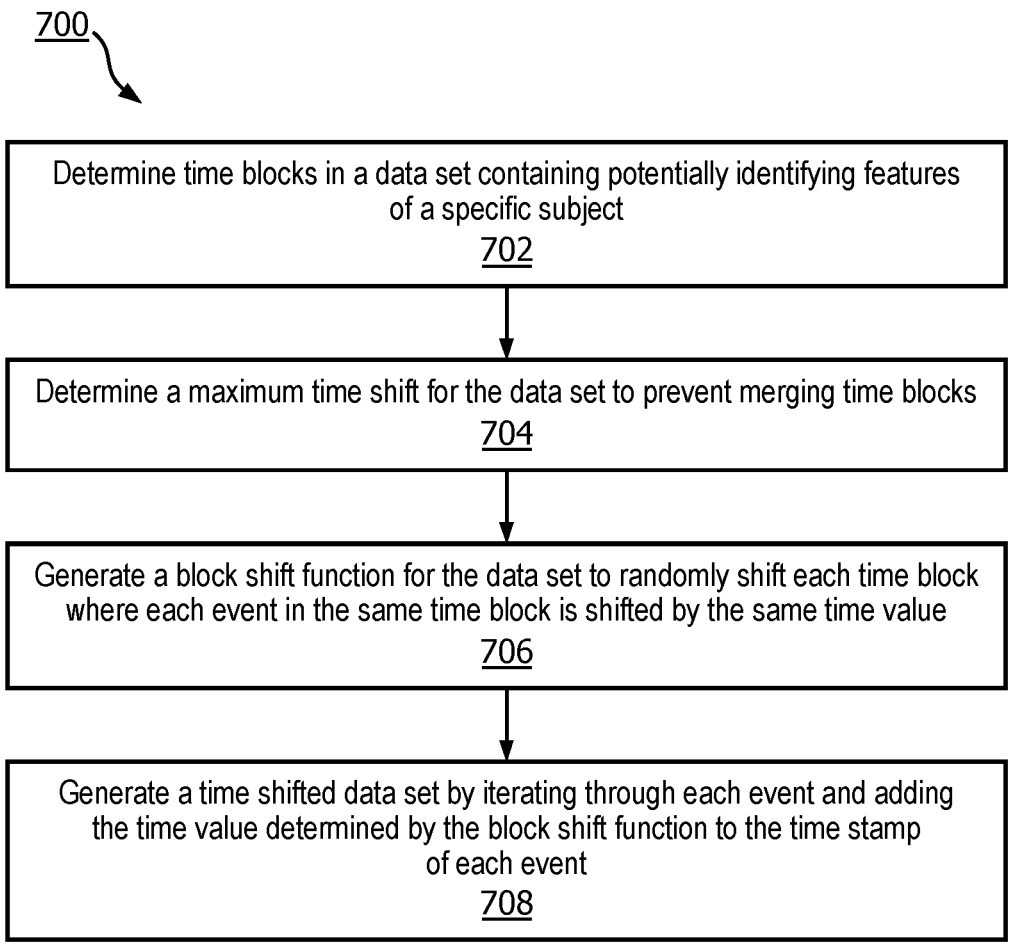
FIG. 7 is a flowchart illustrating another example process for performing selected aspects of the present disclosure, in accordance with an embodiment of the invention.

Referring to FIG. 7, an example process 700 for practicing selected aspects of the present disclosure, in accordance with various embodiments is disclosed. For convenience, the operations of the flowchart are described with reference to a system that performs the operation. This system may include various components of various computer systems, including those described in FIG. 8. Moreover, while operations of process 700 are shown in a particular order, this is not meant to be limiting. One or more operations may be reordered, omitted, and/or added.

At block 702, time blocks in a data set containing potentially identifying features of a specific subject can be determined. In many embodiment, time blocks can be determined using a process similar to process 600 described in FIG. 6.

At block 704, a maximum time shift for the data set can be determined to prevent merging time blocks. In some embodiments, a maximum time shift can be user specified and/or a system default. In many embodiments, the maximum time shift can be no longer than twice the minimum time determined between any two events in the data set.

At block 706, a block shift function can be generated for the data set to randomly shift each time block where each event in the same time block is shifted by the same time value. In many embodiments, block shift functions can constrain the time shift. For example, time shifts can be constrained to a full 24 hours to preserve the time of day of events within the time shifted data set. Additionally or alternatively, time shifts can be constrained to a one week increment to preserve the day of the week in the time shifted data set. In many embodiments, events can occur between time blocks (e.g., a primary care visit between hospital admissions). Randomly generated time shifts of time blocks can be connected with interpolated time differences (e.g., linear interpolation, sinusoidal interpolation, etc.) which can create a piecewise linear block shift function. For example, block shift function 408 in FIG. 4 illustrates an example piecewise linear block shift function which can de-identify raw healthcare data 402.

At block 708, a time shifted data set can be generated by iterating through each event and adding the time value determined by the block shift function to the time stamp of each event. In a variety of embodiments, adding the same time value to each event in a specific time block can preserve relative time data between events within a time block. For example, time shifted de-identified healthcare data 410 can be generated using a piecewise linear block shift function 408. The time shifted de-identified data set can be unmatchable with external data sources.

Figure 8:
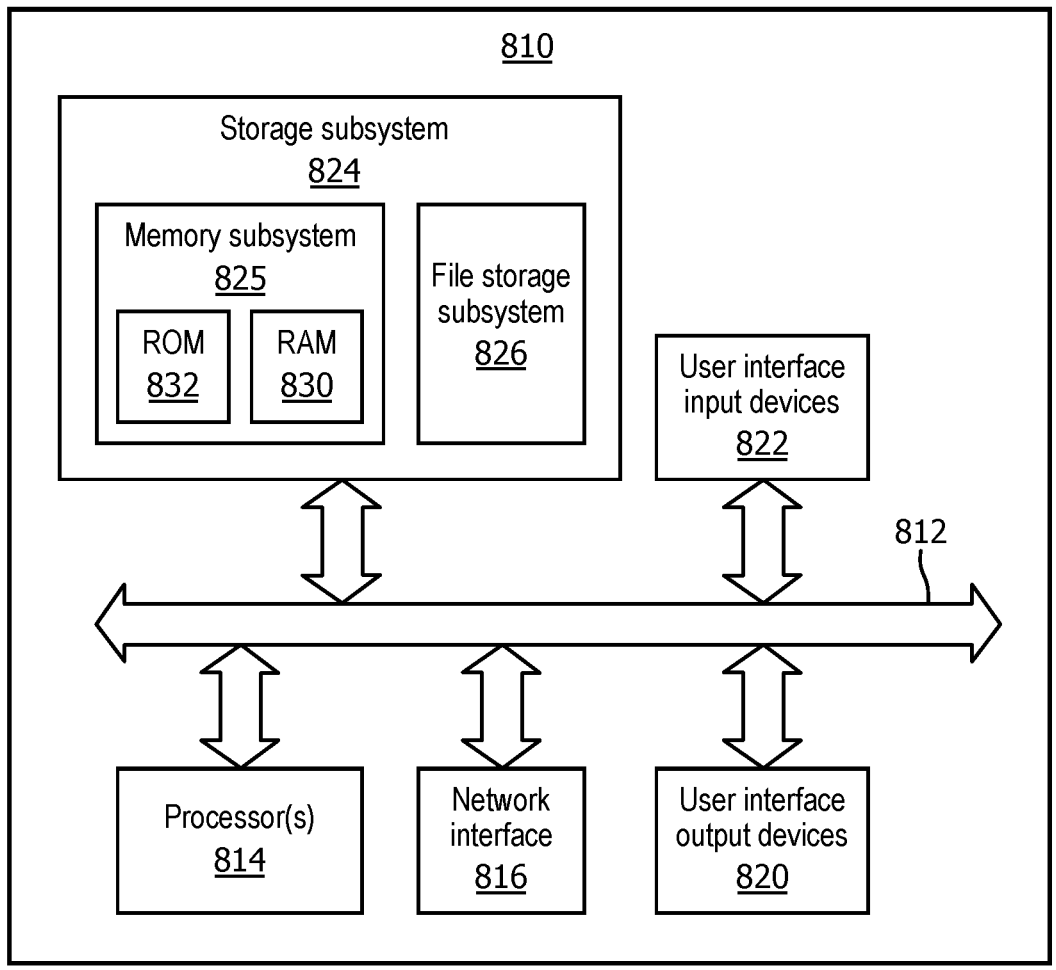
FIG. 8 is a diagram depicting an example computing system architecture, in accordance with an embodiment of the invention.

FIG. 8 is a block diagram of an example computing device 810 that may optionally be utilized to perform one or more aspects of techniques described herein. In some embodiments, one or more of a client computing device, user-controlled resources engine 830, and/or other component(s) may comprise one or more components of the example computing device 810.

Computing device 810 typically includes at least one processor 814 which communicates with a number of peripheral devices via bus subsystem 812. These peripheral devices may include a storage subsystem 824, including, for example, a memory subsystem 825 and a file storage subsystem 826, user interface output devices 820, user interface input devices 822, and a network interface subsystem 816. The input and output devices allow user interaction with computing device 810. Network interface subsystem 816 provides an interface to outside networks and is coupled to corresponding interface devices in other computing devices.

User interface input devices 822 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 810 or onto a communication network.

User interface output devices 820 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 810 to the user or to another machine or computing device.

Storage subsystem 824 stores programming and data constructs that provide the functionality of some or all of the modules described herein. For example, the storage subsystem 824 may include the logic to perform selected aspects of the processes of FIGS. 5-7.

These software modules are generally executed by processor 814 alone or in combination with other processors. Memory 825 used in the storage subsystem 824 can include a number of memories including a main random access memory (RAM) 830 for storage of instructions and data during program execution and a read only memory (ROM) 832 in which fixed instructions are stored. A file storage subsystem 826 can provide persistent storage for program and data files, and may include a hard disk drive, a floppy disk drive along with associated removable media, a CD-ROM drive, an optical drive, or removable media cartridges. The modules implementing the functionality of certain embodiments may be stored by file storage subsystem 826 in the storage subsystem 824, or in other machines accessible by the processor(s) 814.

Bus subsystem 812 provides a mechanism for letting the various components and subsystems of computing device 810 communicate with each other as intended. Although bus subsystem 812 is shown schematically as a single bus, alternative embodiments of the bus subsystem may use multiple busses.

Computing device 810 can be of varying types including a workstation, server, computing cluster, blade server, server farm, or any other data processing system or computing device. Due to the ever-changing nature of computers and networks, the description of computing device 810 depicted in FIG. 8 is intended only as a specific example for purposes of illustrating some embodiments. Many other configurations of computing device 810 are possible having more or fewer components than the computing device depicted in FIG. 8.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

It should also be understood that, unless clearly indicated to the contrary, in any methods claimed herein that include more than one step or act, the order of the steps or acts of the method is not necessarily limited to the order in which the steps or acts of the method are recited.

While the invention has been illustrated and described in detail in the drawings and foregoing description, such illustration and description are to be considered illustrative or exemplary and not restrictive; the invention is not limited to the disclosed embodiments.

What is claimed is:

1. A method implemented with one or more processors to de-identify data associated with a specific subject in a data set, comprising:

obtaining data indicative of the data set, wherein the data set contains, as potential identifying features of the specific subject, multiple bursts of temporally-proximate events;

processing the data indicative of the data set to identify a plurality of time blocks within the data set, wherein each time block in the plurality of time blocks captures one of the bursts of temporally-proximate events for the specific subject;

calculating a random time shift for each time block in the plurality of time blocks, wherein the time shift calculated for each time block adds noise between the each time block and one or more temporally-adjacent time blocks of the plurality of time blocks while preserving temporal relationships between individual events of the temporally-proximate events captured in the respective time block, thereby removing or obfuscating the identifying features of the specific subject from the data set; and generating a time shifted data set by applying the random time shifts to events captured in the plurality of time blocks.

2. The method of claim 1, wherein the time shifted data set is unmatchable with data indicative of an external data source comprising one or more additional identifying features of the specific subject.

3. The method of claim 1, wherein processing the data indicative of the data set to determine the plurality of time blocks further comprises:

determining one or more time gaps using a predetermined threshold time value, where no events in the bursts of temporally-proximate events occur during each gap in the one or more time gaps.

4. The method of claim 3, wherein processing the data indicative of the data set to determine the plurality of time blocks further comprises:

determining a time stamp for each event in the one or more bursts of temporally-proximate events;

determining a first time-stamped event after each gap in the one or more gaps to indicate a start of a time block in the plurality of time blocks;

determining a last time-stamped event before each gap in the one or more gaps to indicate an end of a time block in the plurality of time blocks; and determining each time bock in the data indicative of the data set using the start of the time block and the end of the time block.

5. The method of claim 4, wherein calculating the random time shift for each time block in the plurality of time blocks further comprises determining a maximum time shift size, wherein the maximum time shift size is twice a maximum size between the time stamp for each event in the one or more bursts of temporally-proximate events.

6. The method of claim 5, wherein calculating the random time shift for each block in the plurality of time blocks further comprises interpolating the random time shift for each of the one or more time blocks to generate a block shift function.

7. The method of claim 6, wherein calculating the random time shift for each of the plurality of time blocks further comprises:

processing each time block in the one or more time blocks with the block shift function by iterating through each event in the burst of temporally-proximate events to generate a time shift value for each event; and processing each time block in the plurality of time blocks by adding to each event, the time shift value for each event.

8. The method of claim 6, further comprising adding a same time shift value generated by the block shift function to each individual event in one time block in the plurality of time blocks.

9. At least one non-transitory computer-readable medium comprising instructions that, in response to execution of the instructions by one or more processors, cause one or more processors to de-identify data associated with a specific subject in a data set by performing the following operations:

obtaining data indicative of the data set, wherein the data set contains, as potential identifying features of the specific subject, multiple bursts of temporally-proximate events;

processing the data indicative of the data set to identify a plurality of time blocks within the data set, wherein each time block in the plurality of time blocks captures one of the bursts of temporally-proximate events for the specific subject;

calculating a random time shift for each time block in the plurality of time blocks, wherein the time shift calculated for each time block adds noise between the each time block and one or more temporally-adjacent time blocks of the plurality of time blocks while preserving temporal relationships between individual events of the temporally-proximate events captured in the respective time block, thereby removing or obfuscating the identifying features of the specific subject from the data set; and generating a time shifted data set by applying the random time shifts to events captured in the plurality of time blocks.

10. The at least one non-transitory computer-readable medium of claim 9, wherein the time shifted data set is unmatchable with data indicative of an external data source comprising one or more additional identifying features of the specific subject.

11. The at least one non-transitory computer-readable medium of claim 9, wherein processing the data indicative of the data set to determine the plurality of time blocks further comprises:

determining one or more time gaps using a predetermined threshold time value, where no events in the bursts of temporally-proximate events occur during each gap in the one or more time gaps.

12. The at least one non-transitory computer-readable medium of claim 11, wherein processing the data indicative of the data set to determine the plurality of time blocks further comprises:

determining a time stamp for each event in the one or more bursts of temporally-proximate events;

determining a first time-stamped event after each gap in the one or more gaps to indicate a start of a time block in the plurality of time blocks;

determining a last time-stamped event before each gap in the one or more gaps to indicate an end of a time block in the plurality of time blocks; and determining each time bock in the data indicative of the data set using the start of the time block and the end of the time block.

13. The at least one non-transitory computer-readable medium of claim 12, wherein calculating the random time shift for each time block in the plurality of time blocks further comprises determining a maximum time shift size, wherein the maximum time shift size is twice a maximum size between the time stamp for each event in the one or more bursts of temporally-proximate events.

14. The at least one non-transitory computer-readable medium of claim 13, wherein calculating the random time shift for each block in the plurality of time blocks further comprises interpolating the random time shift for each of the one or more time blocks to generate a block shift function.

15. The at least one non-transitory computer-readable medium of claim 14, wherein calculating the random time shift for each of the plurality of time blocks further comprises:
 processing each time block in the one or more time blocks with the block shift function by iterating through each event in the burst of temporally-proximate events to generate a time shift value for each event;
 processing each time block in the plurality of time blocks by adding to each event, the time shift value for each event.

16. The at least one non-transitory computer-readable medium of claim 14, further comprising adding a same time shift value generated by the block shift function to each individual event in one time block in the plurality of time blocks.

17. A system comprising one or more processors and memory operably coupled with the one or more processors, wherein the memory stores instructions that, in response to execution of the instructions by one or more processors, cause the one or more processors to de-identify data associated with a specific subject in a data set by performing the following operations:
 obtaining data indicative of the data set, wherein the data set contains, as potential identifying features of the specific subject, multiple bursts of temporally-proximate events;
 processing the data indicative of the data set to identify a plurality of time blocks within the data set, wherein each time block in the plurality of time blocks captures one of the bursts of temporally-proximate events for the specific subject;
 calculating a random time shift for each time block in the plurality of time blocks, wherein the time shift calculated for each time block adds noise between the each time block and one or more temporally-adjacent time blocks of the plurality of time blocks while preserving temporal relationships between individual events of the temporally-proximate events captured in the respective time block, thereby removing or obfuscating the identifying features of the specific subject from the data set; and
 generating a time shifted data set by applying the random time shifts to events captured in the plurality of time blocks.

18. The system of claim 17, wherein the time shifted data set is unmatchable with data indicative of an external data source comprising one or more additional identifying features of the specific subject.

19. The system of claim 17, wherein processing the data indicative of the data set to determine the plurality of time blocks further comprises:
 determining one or more time gaps using a predetermined threshold time value, where no events in the bursts of temporally-proximate events occur during each gap in the one or more time gaps.

20. The system of claim 19, wherein processing the data indicative of the data set to determine the plurality of time blocks further comprises:
 determining a time stamp for each event in the one or more bursts of temporally-proximate events;
 determining a first time-stamped event after each gap in the one or more gaps to indicate a start of a time block in the plurality of time blocks;
 determining a last time-stamped event before each gap in the one or more gaps to indicate an end of a time block in the plurality of time blocks; and
 determining each time bock in the data indicative of the data set using the start of the time block and the end of the time block.

* * * * *